US00PP30189P2

(12) United States Plant Patent
Pan

(10) Patent No.: US PP30,189 P2
(45) Date of Patent: Feb. 12, 2019

(54) ***CALENDULA* PLANT NAMED 'CDAZ0002'**

(50) Latin Name: *Calendula maritima*
Varietal Denomination: CDAZ0002

(71) Applicant: SYNGENTA PARTICIPATIONS AG, Basel (CH)

(72) Inventor: Shifeng Pan, Gilroy, CA (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/731,612

(22) Filed: Jul. 7, 2017

(51) Int. Cl.
*A01H 5/02* (2018.01)

(52) U.S. Cl.
USPC ..... Plt./263.1

(58) Field of Classification Search
USPC ..... Plt./263.1
See application file for complete search history.

*Primary Examiner* — Susan McCormick Ewoldt
(74) *Attorney, Agent, or Firm* — Dale Skalla

(57) ABSTRACT

A new cultivar of *Caledula* plant named 'CDAZ0002' particularly distinguished by apricot orange flower color and double flower form.

1 Drawing Sheet

Latin name of the genus and species of the plant claimed: *Calendula maritima.*

Varietal denomination: 'CDAZ0002'.

BACKGROUND OF THE NEW PLANT

The present invention comprises a new *Calendula*, botanically known as *Calendula maritima*, and hereinafter referred to by the variety name 'CDAZ0002'.

'CDAZ0002' is a product of a planned breeding program. The new cultivar has deep apricot orange flower color and double flower form.

'CDAZ0002' originated from selfing a hybrid plant 'GUC0266-1' made in a greenhouse in June of 2010 in Gilroy, Calif., United States of America. This 'GUC0266-1' plant was developed in our breeding program, unpatented, with orange flower color, double flower, and overall larger size than that of 'CDAZ0002'. 'CDAZ0002' differs from it's sibling 'CDAZ0001' which has a darker orange/yellow bi-colored single flower.

The resultant seed was sown in January 2011 in a greenhouse in Gilroy, Calif., United States.

'CDAZ0002' was selected as one flowering plant within the progeny of the stated cross in March 2011 in Gilroy, Calif.

The first act of asexual reproduction of 'CDAZ0002' was accomplished when vegetative cuttings were propagated from the initial selection. This initial selection took place on Mar. 15, 2017 in Gilroy, Calif.

BRIEF SUMMARY OF INVENTION

Horticultural examination of plants grown from cuttings of the plant initiated in April, 2012 in Gilroy, Calif., and continuing thereafter, has demonstrated that the combination of characteristics as herein disclosed for 'CDAZ0002' are firmly fixed and are retained through successive generations of asexual reproduction.

'CDAZ0002' has not been observed under all possible environmental conditions. The phenotype may vary significantly with variations in environment such as temperature, light intensity and day length.

A Plant Breeder's Right for this cultivar has not been applied for. 'CDAZ0002' has not been made publicly available prior to the effective filing date of this application, notwithstanding any disclosure that may have been made less than one year prior to the effective filing date of this application by the inventor or another who obtained 'CDAZ0002' directly from the inventor.

The following traits have been repeatedly observed and are determined to be basic characteristics of the new variety. The combination of these characteristics distinguishes this *Calendula* as a new and distinct variety.

BRIEF DESCRIPTION OF THE PHOTOGRAPHS

Figure 1:
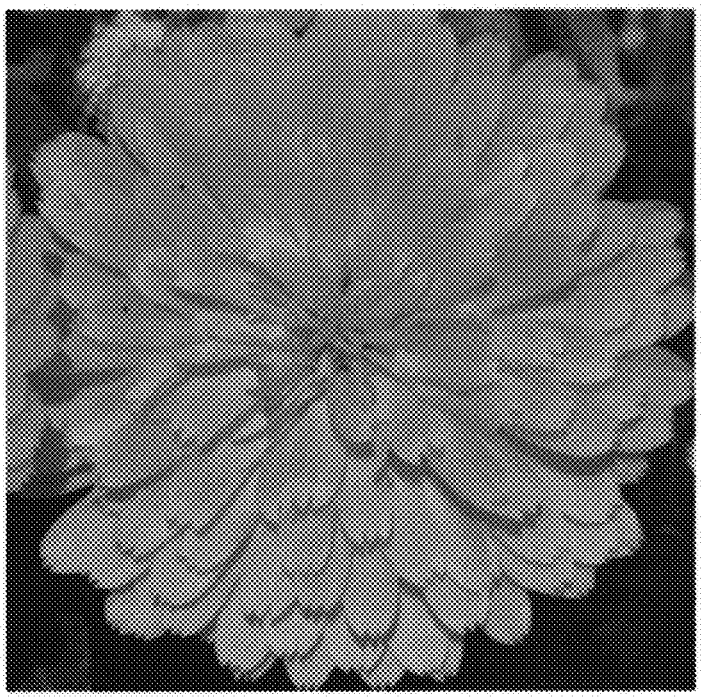
Figure 2:
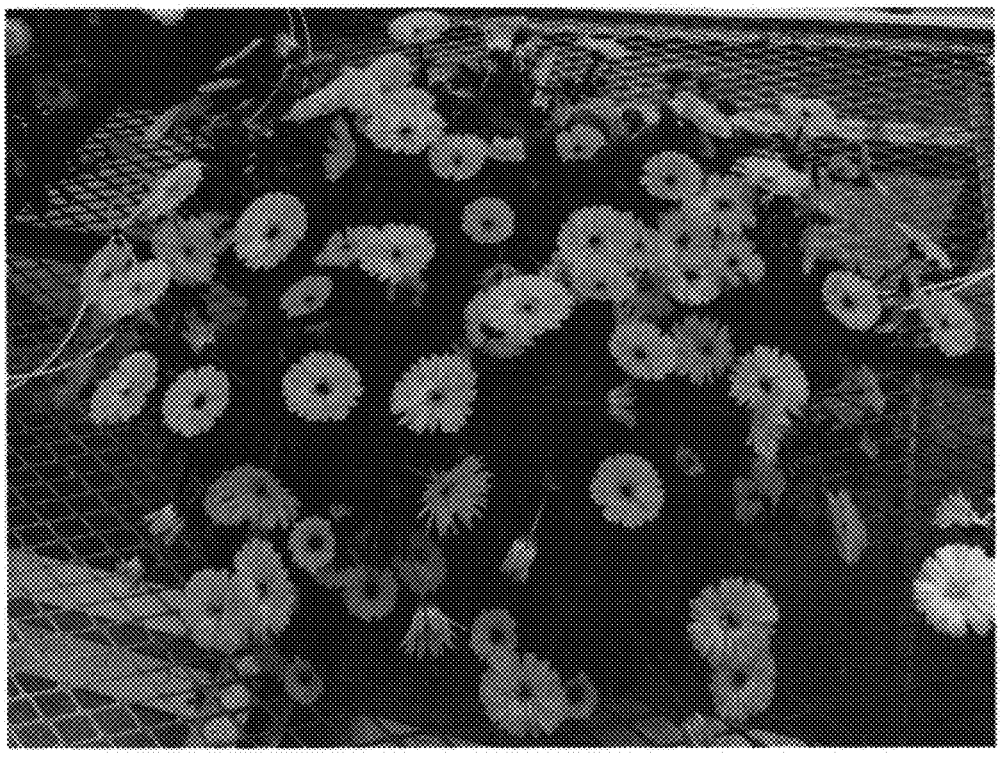

The accompanying photographic drawings show typical flower and foliage characteristics of 'CDAZ0002' with colors being as true as possible with an illustration of this type The photographic drawings show in FIG. 1 a close view of flower of the new variety and in FIG. 2 a flowering plant from an outdoor trial.

The aforementioned photographs: FIG. 1, as well as FIG. 2, were taken in October 2016 both showing a plant from the same natural outdoor trial in Gilroy, Calif. These plants were about 18 weeks of age. One rooted cutting per pot had been planted in a one gallon pot, not pinched in week 22. Plants started flowering end of July.

DETAILED BOTANICAL DESCRIPTION

The measurements were taken in Gilroy, Calif. in May 2017 on the plants from the aforementioned trial.

Color references are made to The Royal Horticultural Society Colour Chart (R.H.S.) 2001.

TABLE 1

DIFFERENCES BETWEEN THE NEW VARIETY CDAZ0002' AND A MOST SIMILAR VARIETY

| | CDAZ0002' | 'SummerLovers Skyfire Yellow' (U.S. Plant Pat No. 15,034) |
|---|---|---|
| Flower color: | Darker orange color | Lighter yellow color |
| Flower size: | Bigger flower | Smaller flower |
| Plant habit or size: | Relatively less plant width and more mound plant habit compared to 'SummerLovers Skyfire Yellow' | Relatively wider and therefore less mound plant habit compared to 'CDAZ0002' |
| Frost tolerance: | Frost tolerant | Frost tolerant |
| Flower shape: | Double round flower | Single flower |
| Plant habit or size: | Larger mound spreading plant | Smaller flat spreading plant |

Plant:

*Form, growth and habit*.—Herbaceous perennial or annual depending on conditions. Compact with strong stems and thick leaves.

*Plant height* (*above soil*).—26-29 cm.

*Plant height* (*inflorescence included*).—29-32 cm.

*Plant width*.—80-90 cm.

Roots:

*Number of days to initiate roots*.—About 4 days at about 22 degrees C.

*Number of days to produce a rooted cutting*.—14-16 days at 22 degrees C.

*Type*.—Fine, fibrous, free branching.

*Color*.—RHS N155B but whiter.

Foliage:

*Leaf shape*.—Narrow oblanceolate to narrow oblong.

*Leaf division*.—Simple.

*Leaf base*.—Truncate, decurrent.

*Leaf apex*.—Acuminate.

*Leaf venation*.—Pinnate, color: upper surface: RHS 147D, lower surface: RHS 144B.

*Leaf margins*.—Entire, with short hairs on the edges.

*Leaf attachment*.—Decurrent.

*Leaf arrangement*.—Alternate.

*Leaf size*.—4.5 cm in length and 1.3-1.5 cm in width.

*Leaf color*.—Young upper surface: RHS NN137A, Young lower surface: RHS 137A, Mature upper: RHS 137A, Mature lower: RHS 137B.

*Leaf surface*.—Upper surface is moderately glossy and slightly rough to the touch, very sparsely covered with very short strigose hairs average of 0.3 mm in length and too small to measure color, lower surface is slightly glossy and slightly rough to the touch.

*Petioles*.—No petioles present, leaves are decurrent.

Stem:

*Shape*.—Rounded.

*Stem color*.—RHS 137C.

*Stem size*.—Length=11.5-14.5 cm, Diameter=3-5 mm.

*Stem strength*.—Strong/flexible.

*Stem aspect*.—Lateral stems grow in an angle of 45° to the main stem.

*Stem surface*.—Moderately glossy, sparsely covered with very short hairs; 0.3 mm in length and too small to measure color.

*Stem number*.—5-6 lateral branches.

*Internode length*.—Average of 2-5 cm in length

*Branching*.—Branches grow from base. .

Inflorescence:

*Inflorescence type*.—Terminal capitulum consisting of ray florets.

*Inflorescence number*.—Average of 1 per lateral stem.

*Inflorescence fragrance*.—Daisy smell.

*Inflorescence aspect*.—Straight on top of stem.

*Inflorescence longevity*.—A few weeks.

*Inflorescence diameter*.—6 cm.

*Inflorescence height*.—2 cm.

*Inflorescence buds*.—Bud length=1.0-1.2 cm, Bud diameter=1.0-1.2 cm, Bud color=RHS 23A.

*Receptable*.—Flattened globular in shape, Diameter=3-5 mm, Height=2 mm, Color=RHS 145A.

*Peduncle*.—Length=4-6 cm and Diameter=2 mm, Color=RHS 138A terminal peduncle is straight on top of stem, moderate strength, surface is glabrous and slightly glossy and moderately covered with short soft hairs.

*Involucral bracts*.—Bracts=25, Upper color=RHS 136A, Lower color=RHS 137A, Length=8 mm, Width=2 mm, arranged in 2 rows, lanceolate in shape, narrowly acute apex, cuneate base, margin entire, upper surface is glabrous, lower surface is densely covered with very short pubescence.

*Number*.—Average of 100-120.

*Arrangement*.—Rotate, 6 whorls.

*Shape*.—Oblanceolate.

*Aspect*.—Slightly upright at the base, held in an average angle of 30°, whole ray floret near horizontal.

*Ray floret apex*.—Praemorse.

*Ray floret base*.—Narrow cuneate.

*Ray floret margins*.—Entire.

*Ray floret surface*.—Upper surface is glabrous and velvety, lower surface is slightly glossy and slightly velvety.

*Ray floret margins*.—Entire.

*Ray floret surface*.—Upper surface is glabrous and velvety, lower surface is slightly glossy and slightly velvety.

*Ray floret color*.—Ray floret=41-48 cm depending on the maturity of the flower (double flower), Length=1.8-2.0 cm, Width=4-5 mm, Upper color=RHS N25C, Lower color=RHS N25C.

*Disc florets*.—~36 disc florets, Base color=RHS 145C, Apex color=RHS 53A.

Reproductive organs:

*Gynoecium*.—1 pistil per ray floret, 4 mm in length, stigma unequal decurrent and RHS 165A to RHS 166A color, style is 2 mm in length and RHS 9B in color, ovary RHS 150D in color.

*Androecium*.—No stamens present.

*Fruit and seed*.—N/A.

What is claimed is:

1. A new and distinct variety of *Calendula* plant named 'CDAZ0002' substantially as illustrated and described herein.

* * * * *